United States Patent [19]

Hobo et al.

[11] 4,260,377
[45] Apr. 7, 1981

[54] DENTAL ARTICULATOR

[75] Inventors: Sumiya Hobo, Tokyo; Nobuhiro Shioda, Tochigi, both of Japan

[73] Assignee: Shioda Dental Manufacturing Co., Ltd., Nasu, Japan

[21] Appl. No.: 31,396

[22] Filed: Apr. 19, 1979

[30] Foreign Application Priority Data

Apr. 22, 1978 [JP] Japan ................ 53-53963[U]

[51] Int. Cl.³ .............................. A61C 11/00
[52] U.S. Cl. ..................................... 433/58
[58] Field of Search ................. 433/58, 64, 57

[56] References Cited

U.S. PATENT DOCUMENTS

| | | | |
|---|---|---|---|
| 3,073,030 | 1/1963 | Gibson et al. | 433/58 |
| 3,159,915 | 12/1964 | Beu et al. | 433/57 |
| 3,624,906 | 8/1969 | Granger | 433/57 |
| 3,908,271 | 9/1975 | Derda et al. | 433/58 |

OTHER PUBLICATIONS

"Occlusomatic" by Hobo, 1977.

Primary Examiner—Robert Peshock
Assistant Examiner—John J. Wilson
Attorney, Agent, or Firm—Stevens, Davis, Miller & Mosher

[57] ABSTRACT

A dental articulator comprises a lower jaw member having a pair of condylar elements and a pair of upwardly extending arms, and an upper jaw member having a pair of glenoid cavities, each condylar element being held in each of the glenoid cavities to articulate the upper and lower jaw members, wherein a pair of condylar shafts for supporting a pair of condylar elements are mounted on the free ends of the arms in horizontal and inward directions.

3 Claims, 9 Drawing Figures

DENTAL ARTICULATOR

This invention relates to an articulator, and, more particularly, to a dental articulator for use in fabrication of dentures or prosthodontics.

An articulator is fundamentally required to have the ability to represent jaw movements as precise as possible, and therefor conventional attempts have been made to improve the capability of representation. Since the capability of representation of the articulator is generally dependent on its adjustability, it has been proposed to incorporate various kinds of adjusting mechanisms in the articulator. The provision of adjusting mechanisms makes it possible to make articulator movements which are closely resemble jaw movements found in the human anatomy, but results in a very complicated articulator construction and operational difficulties.

Thus, such an articulator with many adjusting mechanisms is not easily operated and quickly adjusted.

In order to eliminate the above disadvantages it has recently been proposed to simplify an articulator construction without deterioration of the capability of representation of the articulator. For example, there has been proposed a simplified articulator having a construction shown in FIGS. 1 to 3, in which a pair of upwardly extending condylar shafts 4 are mounted on a top bar 2 of a lower jaw member 1, and wherein a pair of condylar elements 3 mounted on the condylar shafts 4 are held under the influence of a centric latch 8 in mechanical glenoid cavities 6 located in an upper jaw member 5. However, such an articulator has serious disadvantages on operations such that an opening angle $\theta$ between the upper and lower jaw members 1 and 5 is restricted by the condylar shafts 4, and that the upper and lower jaw members are apt to be separated from one another during the operations. To be concrete, when opening the upper and lower jaw members, the upper or lower jaw member has to be rotated around a lateral axis of rotation passing through the centers of the condylar elements 3. In the above construction, however, when the upper jaw member is rotated, the lowermost edges 7 of posterior walls of the mechanical glenoid cavities 6 are brought into contact with the condylar shafts 4 as shown in FIG. 3, resulting in the restriction of the opening angle $\theta$. In the practical and clinical applications of the articulator, it is frequently required to open the upper and lower jaw members at an angle not less than 130°. In order to open the upper and lower jaw members of the above articulator more widely, it is necessarily required to remove the centric latch 8, which is fitted in a centric and posterior notch 10 of the upper jaw member 5, to allow the upper jaw member to be separated from the lower jaw member 1. Further, the condylar elements 3 are held in the glenoid cavities 6 only by the slight pushing force of the centric latch 8, the upper and lower jaw members are apt to be separated from one another by eccentric movements, i.e., horizontal rotational movements (about 15°) around the left or right condylar element 3, or opening and closing movements, or forward and backward movements during the operation of the articulator. In addition, it is difficult to maintain the centric latch 8 at a centric position.

It is therefore an object of the present invention to provide an articulator which overcomes the aforesaid disadvantages and has a simple construction, dependability and excellent operatability.

Another object of the present invention is to provide an articulator wherein relative movements between upper and lower jaw members closely resemble that found in the human anatomy.

According to the present invention there is provided an articulator comprising a lower jaw member having a pair of condylar elements and a pair of upwardly extending arms, and an upper jaw member having a pair of glenoid cavities, each of said condylar elements being held in each of said glenoid cavities to articulate the upper and lower jaw members, wherein a pair of condylar shafts for supporting a pair of condylar elements are mounted on the free ends of the arms in horizontal and inward directions.

According to the preferred embodiment of the present invention, each condylar element is held in a glenoid cavity of the upper jaw member under the pressure of spring means mounted on the upper jaw member.

Preferably, the articulator is so designed that the condylar element may be released from the pressure of spring means by actuating a release lever which is mounted on the upper jaw member so as to be in contact with the spring means.

These and other objects, features and advantages of the present invention will be fully understood from the detailed description taken in conjunction with the accompanying drawings which are by way of illustration only and thus are not limitative of the present invention, and wherein.

Figure 1:
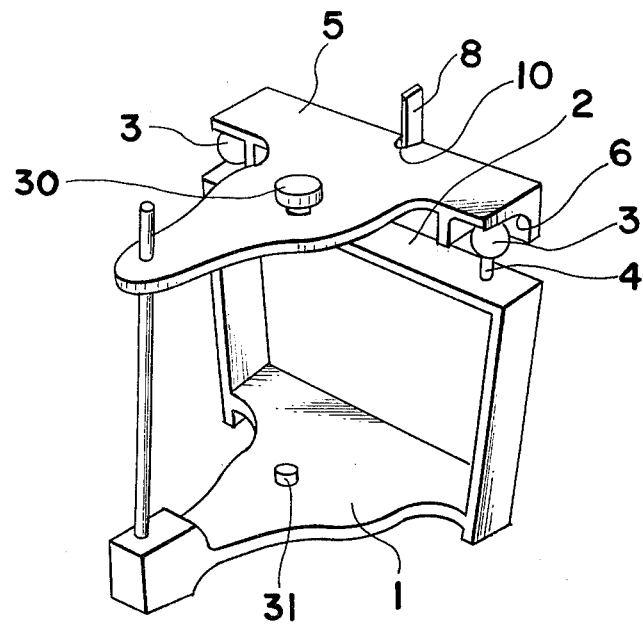
FIGS. 1, 2 and 3 illustrate in a perspective view, fragmentary front elevation and fragmentary side elevation of a prior art articulator.
Figure 2:
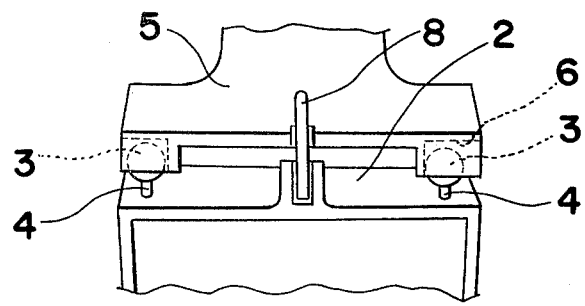
Figure 3:
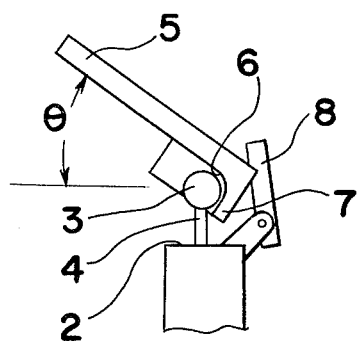
Figure 4:
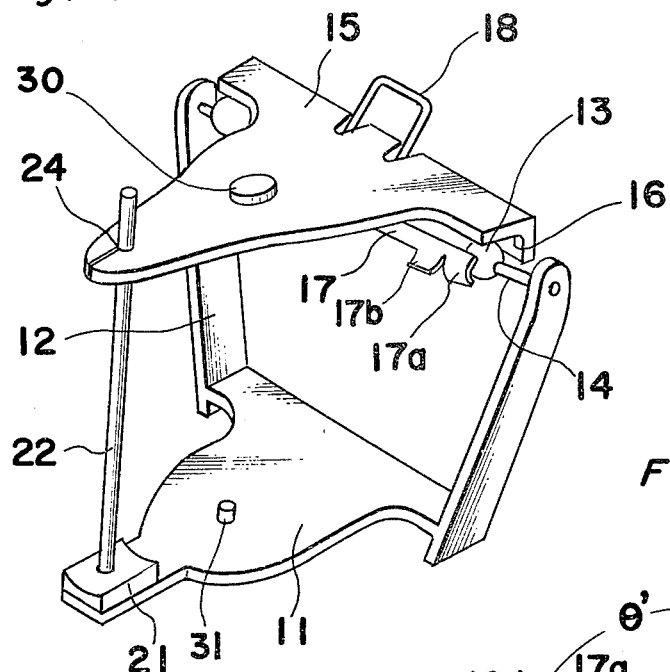
FIG. 4 is a perspective view of the articulator of the present invention.

Referring now to the drawings, and particulary FIG. 4, a dental articulator of the present invention comprises a lower jaw member 11 and an upper jaw member 15 to which mandibular and maxillary casts may be attached by thumbscrews 30 and 31. The lower jaw member 11 is provided with a spaced pair of arms 12 extending upwardly from posterior laterals of the lower jaw member in such a manner that a distance between upper ends of the arms 12 is greater than the width of the upper jaw member 15. A pair of condylar shafts 14, on each of which a sphere-shaped condylar element 13 is fixed, are mounted on the upper ends of the arms 12 and extend therefrom in the horizontal and inward directions. On the anterior part of the lower jaw member 11 there is mounted an incisal guide 21 on which an incisal pin 22 may be rested. The incisal pin 22 is mounted in the anterior part of the upper jaw member 15 in the known manner. The means for mounting incisal pin may be a spring clip and screw mechanism. The incisal pin 22 and incisal guide 21 permit the adjustment of the vertical distance between the maxillary and mandibular casts mounted on the upper and lower jaw members.

Figure 5:
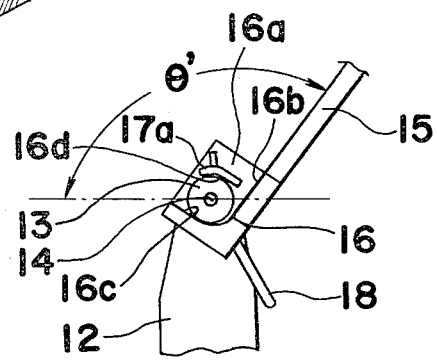
FIG. 5 is a fragmentary sectional side view of the articulator of the present invention.
Figure 6:
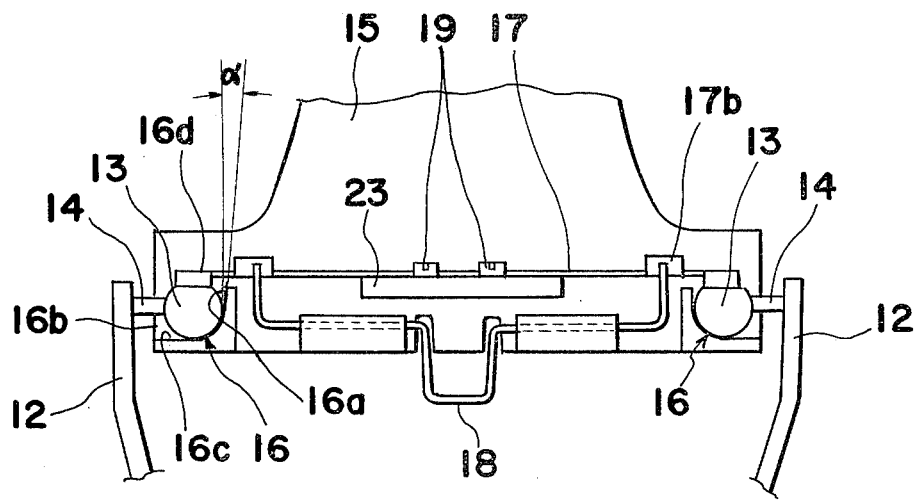
FIG. 6 is a fragmentary front view of the articulator of the present invention in an opened state.
Figure 7:
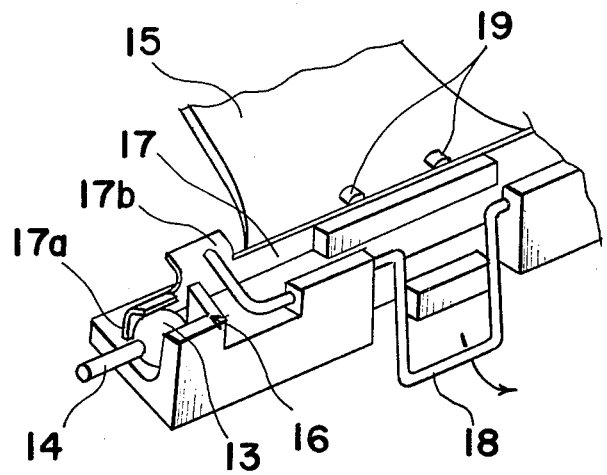
FIG. 7 is a fragmentally perspective view of the essential part of the articulator of the present invention.

As can be seen from FIGS. 6 and 7, the upper jaw member 15 is provided with a spaced pair of mechanical glenoid cavities 16 at its posterior laterals. The glenoid cavities 16, located in the upper jaw member, has medial, superior and posterior walls 16a, 16b, 16c. As shown in FIG. 5, the anterior walls 16d of the glenoid cavities 16 are formed by free ends of a plate spring 17 which is fixed to a mounting member 23 at its central portion by bolts 19, the mounting member 23 being provided on the underside of the upper jaw member 15. Lower parts 17a of the free ends of the plate spring 17 are bent in the posterior directions to support condylar elements 13.

The condylar elements 13 are held in the glenoid cavities 16 to articulate the upper and lower jaw members under the pressure caused by the elasticity of the plate spring 17, permitting the upper and lower jaw members to be opened and closed, yet return to the same position each time. The condylar elements 13 may be released from the pressure received from the plate spring 17, by turning a release lever 18 in the direction indicated by an arrow in FIG. 7, thereby permitting the lower and upper jaw members 11 and 15 to be separated from one another. The release lever 18 is held in horizontal grooves provided in the upper jaw member 15 posteriorly, and is brought into contact with bents 17b of the plate spring 17 at both ends.

In the above articulator construction of the present invention, the plate spring 17 with a suitable elastic strength prevents the separation of the condylar elements 13 from the glenoid cavities 16 during eccentric movements, forward and backward movements, or rotational movements of the articulator in its operation. This simulates the actual human anatomy where dislocation of the mandibular joint is prevented by the elastic tissue such as the articular ligament and joint capsule. Further, the plate spring 17 ensures that the condylar elements 13 may be moved under pressure along the interior walls of the glenoid cavities during the eccentric movements, or forward and backward movements of the articulator.

As described above, the condylar shafts 14 are horizontally mounted on the arms 12 of the lower jaw member 11, so that they would not hinder the upper jaw member 15 from rotating around the horizontal axis of rotation. Accordingly, the articulator of the present invention makes it possible to open the upper and lower jaw members even at an opening angle $\theta'$ of 180° and the above.

Figure 8:
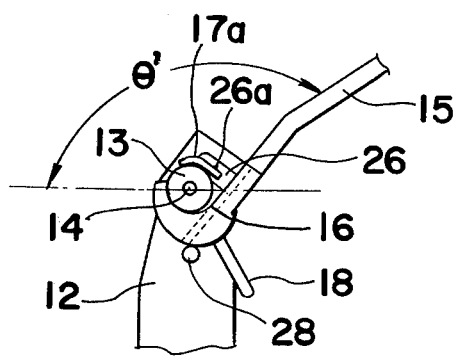
FIG. 8 and 9 are similar to FIGS. 5 and 6, showing a modification of the articulator of the present invention.
Figure 9:
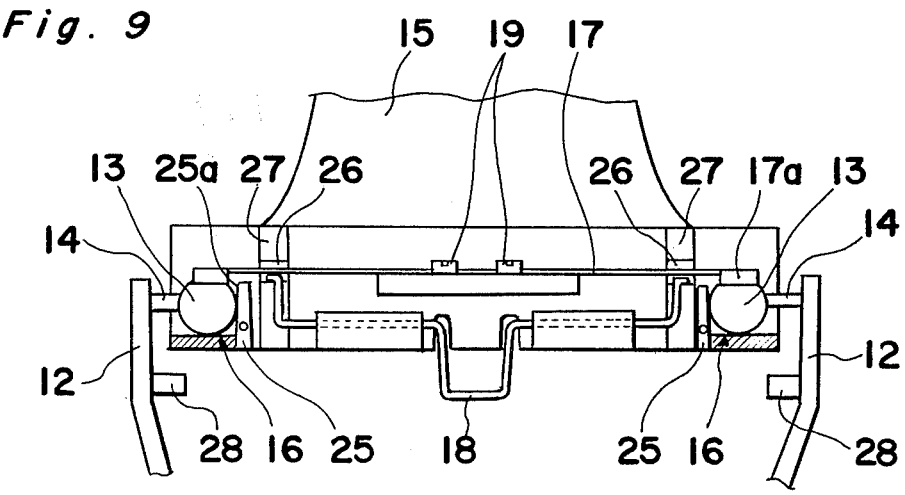

Referring now to FIGS. 8 and 9, there is shown a modification of the articulator of the present invention. In this modification, a pair of sliding members 26 are used instead of the provision of the bents 17b on the plate spring 17. The sliding members 26 having vertical slits 26a are slidably arranged in the grooves 27 provided in the upper jaw member 15, and the plate spring 17 are inserted into the slits 26a. The medial walls of the glenoid cavities 16 may be formed by removable members 25 with inclines 25a to adjust the bennet angle $\alpha$ (cf. FIG. 6). Also, a pair of stoppers 28 may be provided on the arms 12 to restrict the opening angle $\theta'$ to a desired angle not less than 130°.

Although the present invention has fully been described by way of the examples with reference to the accompanying drawings, it is to be noted that various changes and modifications will be apparent to those skilled in the art. Such changes and modification, unless they depart from the spirit and scope of the present invention, are to be construed as being included within the scope of the present invention.

What we claim is:

1. A ball and box type Arcon dental articulator comprising a lower jaw member provided with a spaced pair of arms extending upwardly from its posterior laterals, an upper jaw member provided with a spaced pair of glenoid cavities at its posterior laterals, a pair of condylar shafts mounted on the free ends of said arms in horizontal and inward directions, a pair of condylar elements respectively mounted on said condylar shafts, and a spring means fixed to said upper jaw member at its central portion, anterior walls of said glenoid cavities, being formed by the free ends of said spring means, each of said condylar elements being held in the glenoid cavities to articulate said upper and lower jaw members under the pressure of said spring means, thereby permitting the upper and lower jaw members to be opened and closed, yet return to the same position each time.

2. The dental articulator of claim 1 comprising means for releasing the condylar elements from the pressure received from said spring means, said means for releasing the condylar elements comprising a release lever rotatably mounted on the posterior of the upper jaw member and being in contact with the spring means at its both ends.

3. The dental articulator according to claim 1 comprising means for releasing the condylar elements from the pressure received from the spring means, said means for releasing the condylar elements comprising a release lever turnably mounted on the posterior of the upper jaw member and a pair of sliding members having vertical slits into which said spring means is inserted, said sliding members being slidably arranged in grooves provided in the upper jaw member, said release lever being in contact with the sliding members at its both ends.

* * * * *